US005757978A

United States Patent [19]
Flick et al.

[11] Patent Number: 5,757,978
[45] Date of Patent: May 26, 1998

[54] METHOD AND SYSTEM FOR DETECTING LOCALIZED BIREFRINGENCE DEFECTS IN A DYNAMIC GLOBAL BIREFRINGENCE FIELD

[75] Inventors: Keith Alan Flick, Sylvania, Ohio; Craig Lyle Mahaney, Milan, Mich.

[73] Assignee: Medar, Inc., Farmington Hills, Mich.

[21] Appl. No.: 683,192

[22] Filed: Jul. 18, 1996

[51] Int. Cl.⁶ .......................... G06K 9/00; G01J 4/00
[52] U.S. Cl. .......................... 382/260; 356/367
[58] Field of Search .......................... 382/260, 263, 382/264; 356/364, 365, 366, 367; 250/255

[56] References Cited

U.S. PATENT DOCUMENTS

| | | | |
|---|---|---|---|
| 4,973,163 | 11/1990 | Sakai | 356/367 |
| 5,146,438 | 9/1992 | Harper | 369/13 |
| 5,257,092 | 10/1993 | Noguchi et al. | 356/367 |
| 5,644,562 | 7/1997 | De Groot | 356/357 |

*Primary Examiner*—Thomas D. Lee
*Attorney, Agent, or Firm*—Brooks & Kushman P.C.

[57] ABSTRACT

A method and system are provided for reliably detecting localized birefringence defects of an object such as an optical media substrate in a dynamic local birefringence field created during cooling of the optical media substrate at an inspection station. A birefringence digital filter filters out high frequency defect data while eliminating background birefringence data in a digital image created by a camera adapted to respond to the birefringence of the optical media substrate under control of a computer. Resulting filtered high frequency defect data is then processed to determine the localized birefringence defects in real-time. In one embodiment, the birefringence digital filter includes an addressable storage device such as a PROM which stores a lookup table which is able to produce filtered data in real-time at a data rate in excess of 8 million pixels per second. In another embodiment, a finite impulse response (FIR) filter, including registered multiplier-adders may be used to calculate or obtain filtered data at a higher rate (i.e. 10 million pixels per second). The filtered data may be post processed to accomplish gain and offset correction as well as to impose nonlinear characteristics on the output data if desired to implement a data squelch. The data squelch can reduce undesirable noise generated as an artifact of the filtering process.

18 Claims, 5 Drawing Sheets

METHOD AND SYSTEM FOR DETECTING LOCALIZED BIREFRINGENCE DEFECTS IN A DYNAMIC GLOBAL BIREFRINGENCE FIELD

TECHNICAL FIELD

This invention relates to method and systems for detecting localized birefringence defects and, in particular, to method and systems for detecting localized birefringence defects in a dynamic global birefringence field.

BACKGROUND ART

As is well known, it is important to detect local birefringence defects in objects such as optical media substrates such as optical discs and, in particular, with respect to magneto optical discs. Such detection is typically done on-line shortly after the optical media substrate has been molded. However, as the substrate cools, the global birefringence field of the substrate changes. Consequently, when the substrate reaches an inspection station such as a machine vision inspection station, it has not yet reached thermoequilibrium. In order to detect local birefringence defects, it is necessary to filter out the dynamic global birefringence field. Such detection is typically accomplished with a camera or image processing board which then passes a processed digital image to a computer.

One potential solution is to use a high pass filter to filter the dynamic global birefringence field from the digital image. However, this is not easy since the frequency difference between the background birefringence field and the defect data is small and the processing needs to be done in real-time (8 MHz pixel rate or higher).

SUMMARY OF THE INVENTION

An object of the present invention is to provide a method and system for detecting localized birefringence defects in a dynamic global birefringence field in real-time.

Another object of the present invention is to provide a method and system for detecting localized birefringence defects in a dynamic global birefringence field by using digital filtering techniques in real-time.

In carrying out the above objects and other objects of the present invention, a method is provided for detecting localized birefringence defects of an object in a dynamic global birefringence field. The method includes the steps of generating a digital image of the object to obtain a signal having high frequency defect data and background birefringence data having a frequency less than the high frequency of the defect data. The method also includes the step of filtering the signal to pass the high frequency defect data while eliminating the background birefringence data. Finally, the method includes the step of processing the high frequency defect data to determine the localized birefringence defects in real-time.

Preferably, the step of filtering is accomplished digitally.

Also, preferably, the step of filtering is accomplished in hardware, such as by an FIR filter or an addressable storage device wherein the real-time data rate of the hardware has a large advantage over prior software-based methods.

The output data of the FIR filter is typically post-processed to accomplish gain and offset correction as well as imposing nonlinear characteristics on the output data if desired. These nonlinear characteristics can be used to implement a data squelch wherein the data squelch is also preferably implemented in hardware and can reduce undesirable noise generated as an artifact of the filtering process.

Further in carrying out the above objects and other objects of the present invention, a system is provided for carrying out each of the above method steps.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 3 is a graph of a sample camera scan showing a local birefringence defect which is circled with the filter of FIG. 2a;

FIG. 4 is a graph showing the sample camera scan after filtering and offset correction with the filter of FIG. 2a;

FIG. 5 is a graph of a magnified view contained within the circle of FIG. 4 illustrating undesired filter artifacts with the filter of FIG. 2a;

BEST MODE FOR CARRYING OUT THE INVENTION

Figure 1:
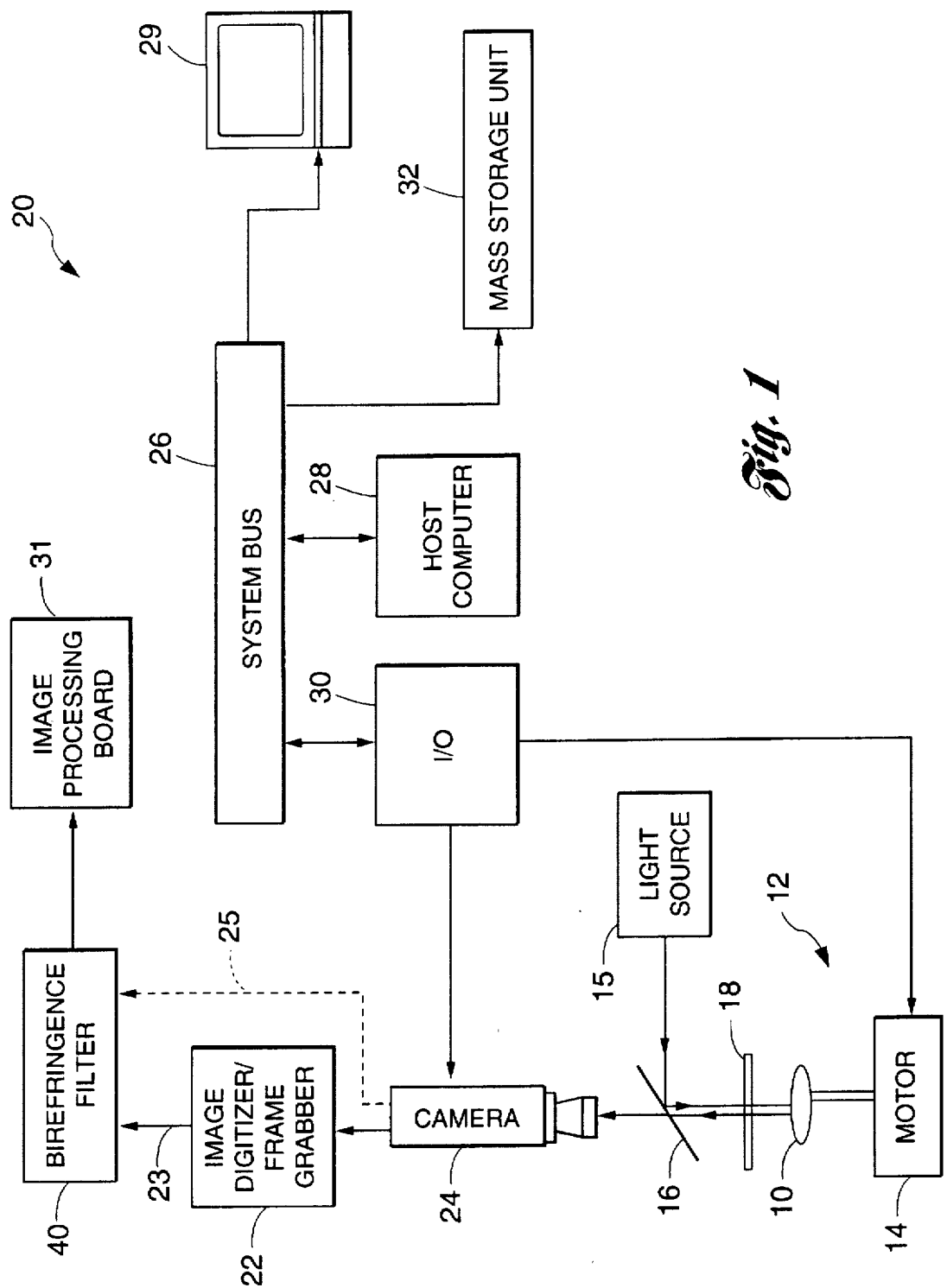
FIG. 1 is a block diagram of a machine vision system capable of carrying out the method and system of the present invention.

Referring to the drawing Figures, there is illustrated schematically in FIG. 1, a machine vision system and station, generally indicated at 20, by which the method and system of the present invention can reliably detect localized birefringence defects of an object in a dynamic global birefringence field. Preferably, the method and system use digital filtering techniques to detect the localized birefringence defects in the dynamic global birefringence field. The object may be an optical media substrate such as an optical or MO disc 10. The dynamic global field exists for a period of time after the optical media substrate 10 has been molded. The field is said to be dynamic because the global field changes as the substrate 10 cools. When the substrate 10 reaches an inspection station 12, it has not yet reached thermal equilibrium.

The machine vision system 20 typically includes an image digitizer/frame grabber 22. The image digitizer/frame grabber 22 samples and digitizes input images from an image source such as a camera 24 along line 23 and places each input image into a frame buffer having picture elements. The image/digitizer/frame grabber 22 may be a conventional frame grabber board such as that manufactured by Matrox, Cognex, Data Translation or other frame grabbers. Alternatively, the image digitizer/frame grabber 22 may comprise a vision processor board such as made by Cognex.

Each of the picture elements may consist of an 8-bit number representing the brightness of that spot in the image. If the camera 24 is a digital camera, the digital camera will eliminate the need for the image digitizer/frame grabber 22 and the input image appears along line 25.

The system 20 also includes input/output circuits 30 to allow the system 20 to communicate with external devices such as a controller (not shown) for controlling a motor such as a stepper motor 14. The disc 10 is rotatably mounted on an output shaft of the motor 14 at the inspection station 12. Typically, the camera 24 scans radially extending portions of the disc 10 as it rotates.

The I/O circuits 30 also allow the system 20 to communicate with a controller (not shown) for controlling the camera 24 at the inspection station 12. The camera 24 may be an image source such as an analog, digital or line scan camera such as RS-170, CCIR, NTSC and PAL.

The inspection station 12 also includes a light source 15 such as a projection lamp, a beam/splitter 16 and a circular polarizer 18 which is typically made from a quarter-wave retarder and a linear polarizer. As is well known, no reflected light passes through the polarizer 18 from the disc 10 if there is no birefringence.

The machine vision system 20 also includes a system bus 26 which may be either a PCI, an EISA, ISA or VL system bus or any other standard bus to allow inter-system communication such as with a monitor 29 of the system 20 or an image processing board 31 as will be described in greater detail hereinbelow.

The machine vision system 20 may be programmed at a mass storage unit 32 to include custom controls for image processing and image analysis.

A host computer 28 of the system 20 may be a PC having a sufficient amount of RAM and hard disk space for computer programs for controlling the system 20.

There is generally indicated at 40 a birefringence digital filter. A first embodiment of the filter 40 is indicated at 40' in FIG. 2 and includes a hardware-based, addressable information storage device 42 (such as a ROM, EPROM, RAM, etc.) which determines an output value of a pixel based on the present and past two input values. Alternatively, the digital filter may comprise a finite impulse response (FIR) filter which computes the output value of a pixel based upon eight of its preceding neighboring pixels on a scan line and is generally indicated at 40" in FIG. 2a.

Figure 2A:
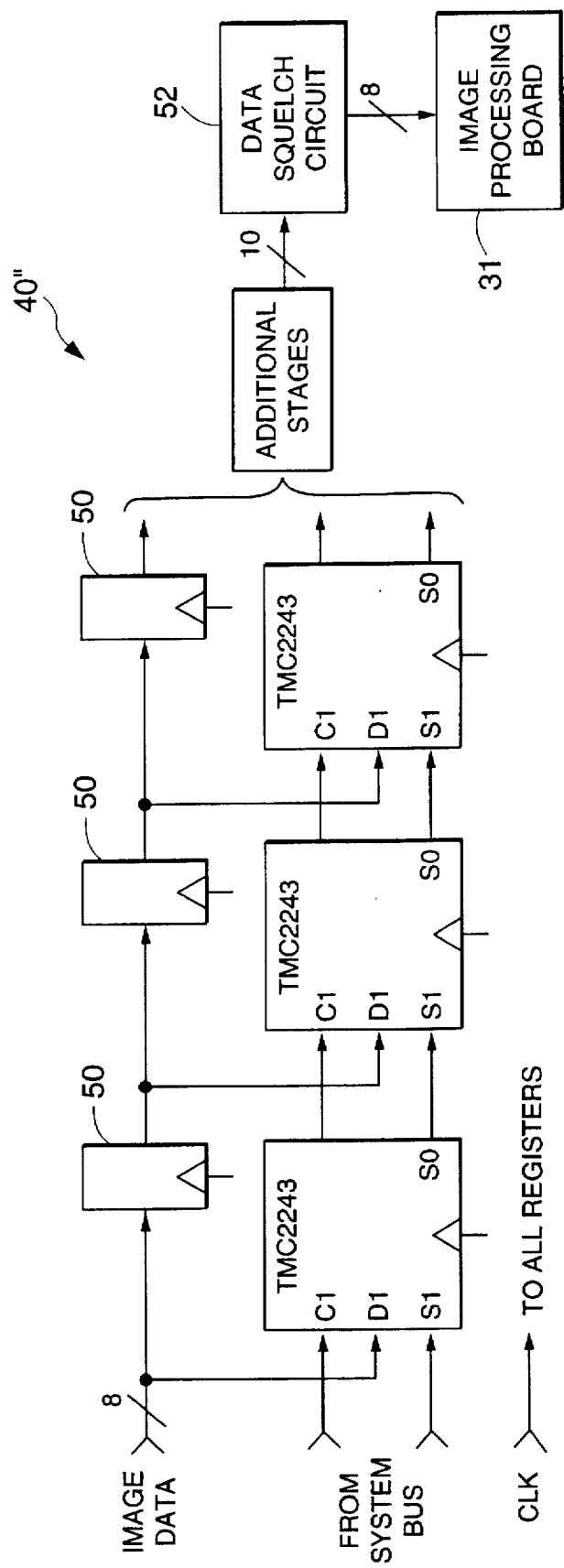
FIG. 2a is a block diagram of another embodiment of a birefringence filter including a squelch circuit of the invention.

The filter 40" of FIG. 2a is able to produce this filtered data in real-time at a data rate of ten million pixels per second. The filter calculations are carried out to a precision of twenty-three bits. The output data of the filter 40" is post processed at a data squelch circuit 52 to accomplish gain and offset correction, as well as impose nonlinear characteristics on the output data if desired. These nonlinear characteristics can be used to implement a data squelch.

The digital filter 40" allows the detection of localized birefringent defects even in the presence of a large dynamic birefringence field. The real-time data rate of the hardware filter 40" has a large advantage over pure software methods. The data squelch, as it is implemented in the hardware by the circuit 52, can reduce undesirable noise generated as an artifact of the filtering process.

In other words, the filter 40" passes the high frequency defects through to the camera processing board 31 while eliminating the not quite so high frequency background birefringence from its input signal. The reason for using the digital filter 40" or the digital filter 40' instead of a high pass filter is that the frequency difference between the background birefringence and the defect data is small and the processing needs to be done in real-time (10 MHz pixel rate for filter 40" and 8 MHz for filter 40').

Figure 2:
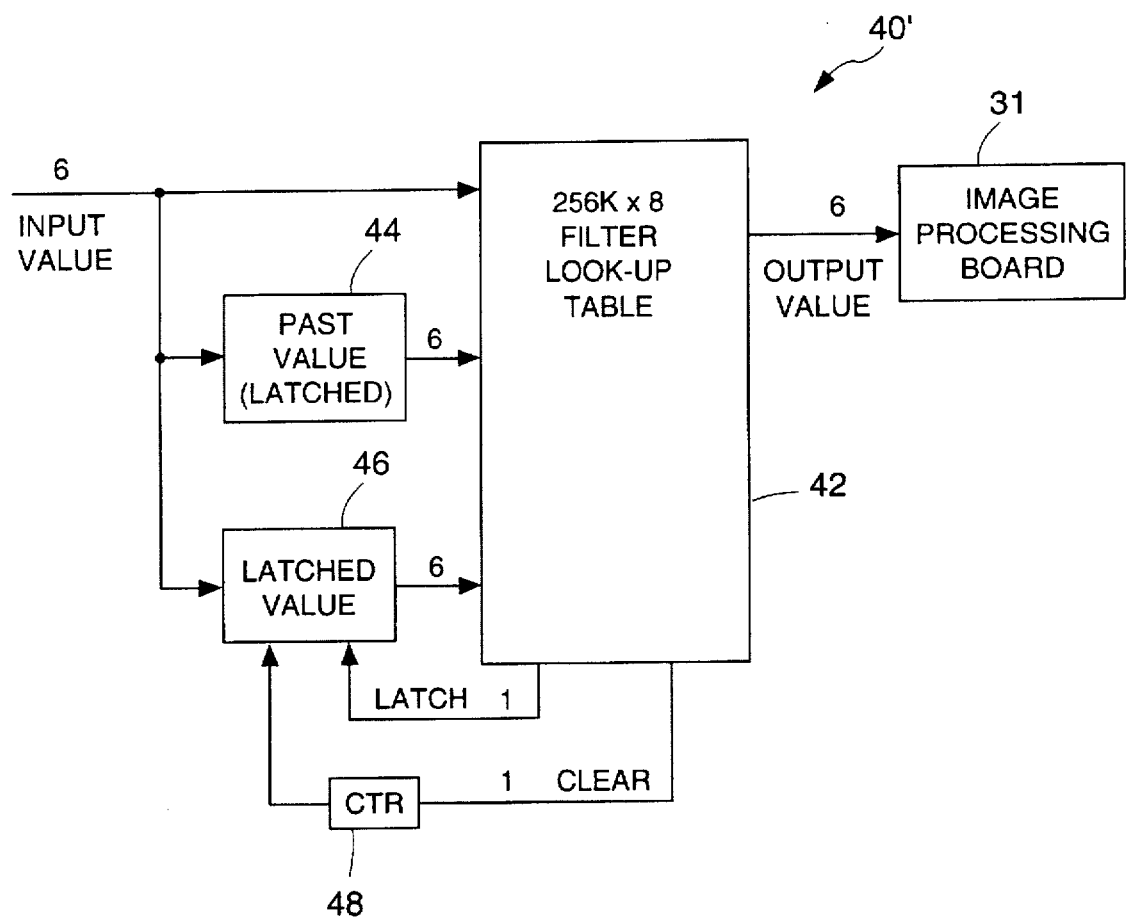
FIG. 2 is a block diagram of one embodiment of a birefringence filter of the present invention.

The digital filter 40 of FIG. 2 includes the device 42 which, when programmed, operates like a lookup table, a past value latch 44, a latched value latch 46 and a counter 48.

The input value is the current digital value in the data stream from the camera 24. This is the value that is saved to both the past value latch 44 (automatically, every pixel) and to the latched value latch 46 (under control of the latch output from the device 42 and the output from the counter 48).

Therefore, the past value latch 44 contains the previous value in the data stream from the camera 24 and the latched value latch 46 contains the most recent value latched from the data stream under the control of the combination of the latch output and the counter output. Both of these values (latched value and previous value) are initialized to the first pixel value at the beginning of the camera data stream.

The output value is the value that is passed to the camera board 31 for processing. (This is the filtered output). The filter 40 may be run in either signed or absolute value mode and the only portion that is different between these two modes is the output value.

The filter table is a large lookup table stored in the device 42 that uses the input value, the past value and the latched value as the address data to the device 42 and the table value to select. The selected table value contains the output value, latch output and a counter clear output.

The birefringence filter 40 preferably uses 6 bit (64 gray scale) values for compatibility with the camera board 31 and is easily modified to handle higher resolution values by increasing the size of the lookup table in the device 42.

A window value is selected according to the noise of the signal, the changes due to the background birefringence and the changes due to the defects to be detected. The window value is a number in gray scale values that is greater than the noise and the background birefringence on a single pixel but is smaller than the defect values on a single pixel.

Referring again to FIG. 1, the basic image processing operation used in the board 31 is a thresholding operation with fixed-valued thresholds. The board 31 will indicate to the host computer 28 whenever the incoming waveform crosses these thresholds. The thresholding operation takes place in real-time at 10 million pixels per second with filter 40".

Referring now to FIG. 2a the filter 40" preferably includes eight (8) clocked pipelined registers 50 (only three of which are shown) which store eight pixel values previous to the current pixel value. Preferably, the digital FIR filter 40" is implemented using Raythen Semiconductor integrated circuits having the designation TMC2243.

The TMC2243 is a video speed three stage 10×10 bit FIR (Finite Impulse Response) filter integrated circuit composed of three registered multiplier-adders concatenated into a one-dimensional systolic array. Utilizing two's complement representation, the TMC2243 accepts one 10-bit data point, updates one 10-bit coefficient, and produces one 16-bit rounded, filtered output point every 50 nanoseconds.

While the TMC2243 accepts one 10-bit data point only, an 8-bit data point is utilized from the image data. The coefficients loaded from the computer 28 are dependent or based on the closeness of the frequencies of the defect data and the background data as well as the type of defect which is to be detected. In this way, the filter 40" determines a filtered current value for a pixel based on its current value minus an average of past values for eight immediately preceding pixels.

The data squelch circuit 52 is preferably implemented with an addressable storage device (i.e. PROM, RAM, ROM) to store a lock-up table to achieve high data rates therethrough.

Figure 3:
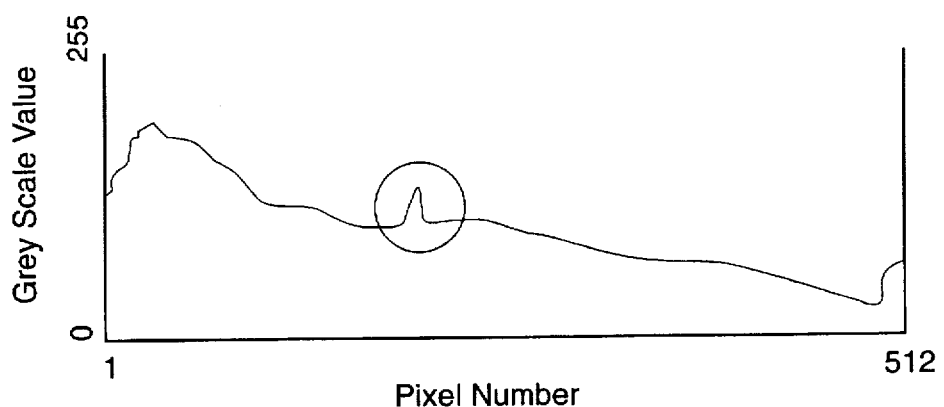

This application presents a problem in that the absolute value of the birefringence waveform of a hot optical storage media substrate 10 changes during inspection. FIG. 3 shows a sample scan line from a 512 pixel camera configured to respond to the birefringence of the optical storage media substrate 10. Notice the presence of a local defect. Consider an absolute value change in the birefringence waveform as choosing a new starting gray scale value for pixel number one in FIG. 3. The filtering process used with the filter 40" and described below is used to return the birefringence waveforms to a common absolute gray scale starting point so as to be detectable with constant valued thresholds.

This waveform is then pipelined (i.e. in parallel) through the filtering operation performed by the filter 40. The filtering algorithm used resembles that of a high pass filter. The raw filter output has both positive and negative valued pixels. Only positive valued pixels are valid for the other image processing hardware in the system. Therefore, a fixed offset is applied to the raw filter output data to give the illusion that gray scale value 128 represents zero. The filter output with offset correction is shown in FIG. 4.

The raw filter output data, being a variation of a high pass filter, will tend to amplify any noise present in the original waveform. The odd and even numbered pixels from the camera 24 traverse separate analog video processing paths, and have an inherent amount of variation between them. This difference is kept to a minimum, but pixel-to-pixel differences of two gray scale levels is not uncommon. When these types of waveforms are filtered as described above, this difference is amplified. A portion of FIG. 4 has been magnified and is shown in FIG. 5.

Figure 6:
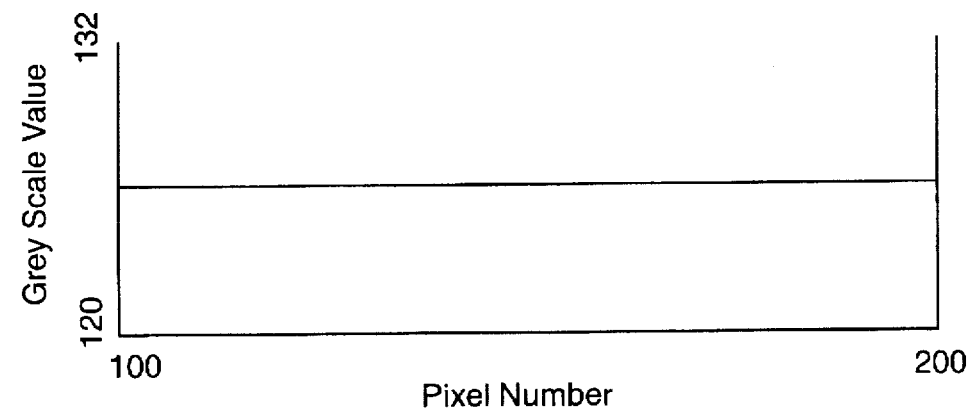
FIG. 6 is a graph of filter noise after data squelch with the filter of FIG. 2A.

As previously mentioned, a data squelch can be used to squelch this noise to a manageable level. The squelch level is completely software programmable. Any pixels whose absolute value from the virtual zero level is below the set point are squelched to the virtual zero level. The pixels having an absolute value from the virtual zero level that exceeds the squelch set point are passed through the squelch unchanged. The effect of the data squelch is shown in FIG. 6.

Figure 4:
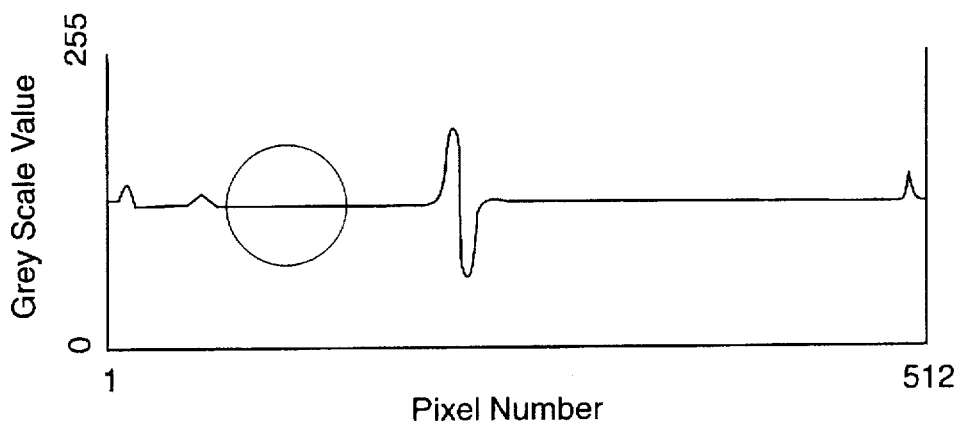
Figure 5:
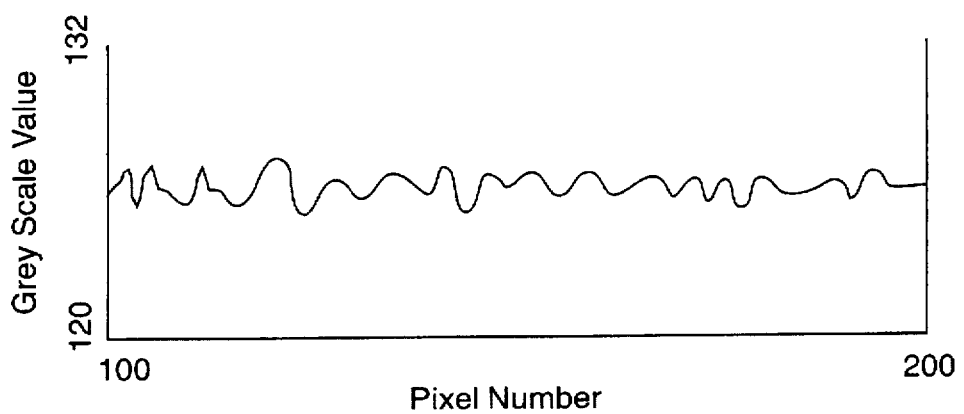

The local birefringence defect originally shown in FIGS. 3 and 4 once having been processed by this custom filter 40" can be passed on to the other image processing hardware in the system. The presence of the local defect is now clearly distinguishable from the other global birefringence by using constant valued thresholds. Additionally, the gray scale output of the filter 40 is now independent of the absolute value of the input waveform.

Theory of Operation of Filter 40'

The theory of operation of the filter 40' is:

If there is a slow change in the signal, everything is updated and the output is a flat line.

If there is a rapid change in the signal the latched value latch 46 saves the gray scale value before the rapid change (defect or flaw) and the output is the difference between the latched value and the input value.

When all three values agree there is now a slow change again everything is updated and the output is again a flat line.

One problem with this logic is that if the birefringence changes the waveform enough over the defective area, the latched value 46 will always be too far from the past value and input value to correct back to a flat line. This is why the counter 48 is part of the filter 40'. Any time the counter 48 is not cleared, the counter 48 will count another pixel. When the counter 48 reaches a predetermined value, it will clear itself and signal the latch 46 to save the input value as the latched value. This happens when the input value and the past value are within the window but the latched value is not. The counter value is chosen so that any defect as large as the counter 48 is a rejectable defect so even if the counter fires on the flat top of a defect, the disc 10 will not be passed incorrectly. For example, see the waveforms of FIGS. 7–10.

Lookup Table Rules

The lookup table 42 is programmed according to the following rules:

If the difference between the latched, past and input values is less than the window value the counter 48 is cleared, the input value is latched into the latched value latch 46 and the output value is 32 for a signed filter and 0 for an absolute value filter.

If the difference(s) between the latched value and either/both the past value and input value is greater than the window value but the difference between the past value and the input value is less than the window value, the latched value is not changed, the counter 48 is not cleared and the output value is 32+(input value–latched value) for a signed filter and |input value–latched value| for an absolute value filter. (The formula "|input value–latched value|" means the "absolute value of the difference between the input value and the latched value".)

If the differences between the past value and the input value are greater than the window value, the counter 48 is cleared, the latched value is not changed and the output value is 32+(input value–latched value) for a signed filter and |input value–latched value| for an absolute value filter.

TABLE 1

| Latch-Past | Latch-Input | Past-Input | Latch Output | Counter Clear | Signed Output | Absolute Value Output |
|---|---|---|---|---|---|---|
| Less | Less | Less | Yes | Yes | 32 | 0 |
| Less | Greater | Greater | No | Yes | 32 + (Input − Latched) | \|Latched − Input\| |
| Less | Greater | Less | No | No | 32 + (Input − Latched) | \|Latched − Input\| |
| Less | Less | Greater | No | Yes | 32 + (Input − Latched) | \|Latched − Input\| |
| Greater | Less | Less | No | No | 32 + (Input − Latched) | \|Latched − Input\| |
| Greater | Greater | Greater | No | Yes | 32 + (Input − Latched) | \|Latched − Input\| |

TABLE 1-continued

| Latch-Past | Latch-Input | Past-Input | Latch Output | Counter Clear | Signed Output | Absolute Value Output |
|---|---|---|---|---|---|---|
| Greater | Greater | Less | No | No | 32 + (Input − Latched) | ⌊Latched − Input⌋ |
| Greater | Less | Greater | No | Yes | 32 + (Input − Latched) | ⌊Latched − Input⌋ |

Less = The difference is less than the window value.
Greater = The difference is greater than the window value.

Waveform Examples for Filter 40'

Figure 7:
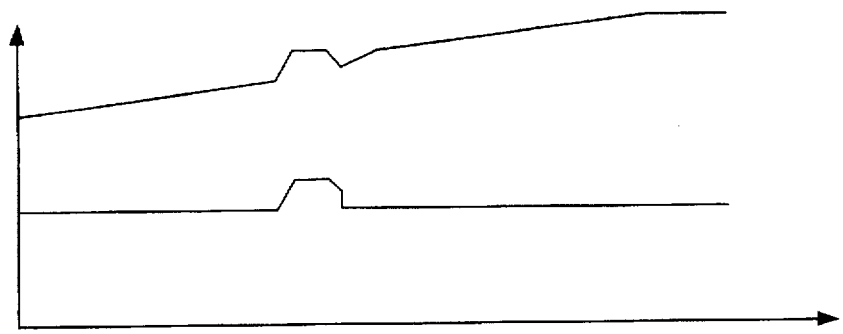
FIG. 7 shows graphs of upper and lower waveforms having a single local birefringence defect wherein the top waveform is the unfiltered value and the bottom waveform is the filtered value and utilizing the filter of FIG. 2.

Referring now to FIG. 7, there is illustrated a first example of a waveform with a single defect that does not have enough background birefringence to change the waveform too much for the latched value, past value and input value to stay within the window value. The top waveform is the unfiltered value and the bottom waveform is the filtered value.

Figure 8:
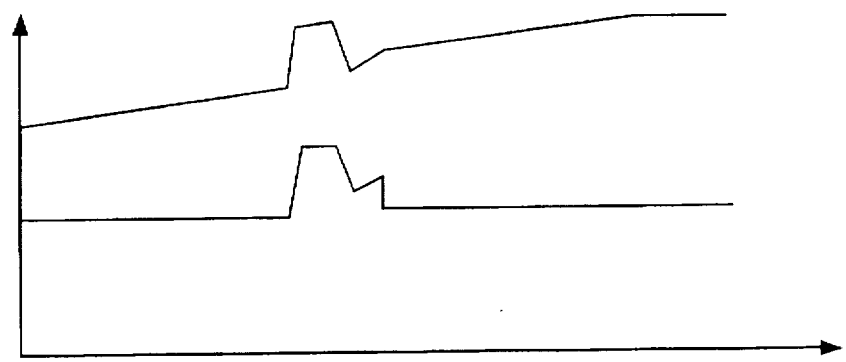
FIG. 8 shows two graphs similar to the graph of FIG. 7 wherein the background or global birefringence field raises the waveforms up and utilizing the filter of FIG. 2.

Referring now to FIG. 8, there is illustrated the result of the background birefringence raising the waveform up to where the latched value cannot be within the window of the past value and the input value. The counter 48 causes the latched value to be updated and this causes the return to the flat signal after a time.

Figure 9:
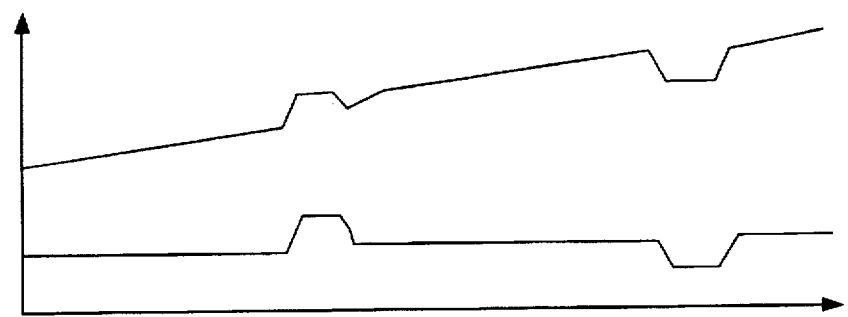
FIG. 9 illustrates graphs similar to the graphs of FIGS. 7 and 8 wherein rising and falling local birefringence defects are illustrated with signed filtering and utilizing the filter of FIG. 2.

Referring now to FIG. 9, this waveform demonstrates both rising and falling defects with signed filtering.

Figure 10:
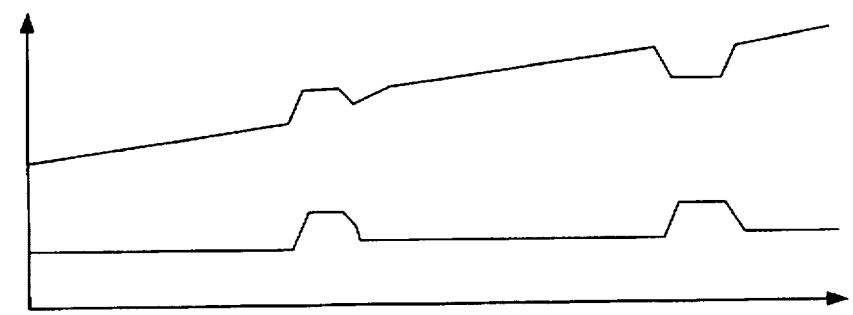
FIG. 10 illustrates graphs similar to the graphs of FIGS. 7, 8 and 9 wherein the lower waveform demonstrates the same input signal with absolute value filtering with the filter of FIG. 2.

Referring now to FIG. 10, the waveform demonstrates the same input signal with the absolute value filtering the absolute value defects only go up from the waveform and not both up and down. This allows the board 31 to detect both types of defects with simpler measures.

While the best mode for carrying out the invention has been described in detail, those familiar with the art to which this invention relates will recognize various alternative designs and embodiments for practicing the invention as defined by the following claims.

What is claimed is:

1. A method for detecting localized birefringence defects of an object in a dynamic global birefringence field, the method comprising the steps of:
   generating a digital image of the object to obtain a signal having high frequency defect data and background birefringence data having a frequency less than the high frequency of the defect data;
   filtering the signal to pass the high frequency defect data while eliminating the background birefringence data; and
   processing the high frequency defect data to determine the localized birefringence defects in real-time.

2. The method as claimed in claim 1 wherein the object is an optical media substrate.

3. The method as claimed in claim 2 wherein the optical media substrate is an optical disc.

4. The method as claimed in claim 3 wherein the optical disc is an MO disc.

5. The method as claimed in claim 1 wherein the step of filtering is accomplished digitally.

6. The method as claimed in claim 2 further comprising the step of storing a set of filter values and wherein the step of filtering includes the step of retrieving a desired subset of the set of filter values.

7. The method as claimed in claim 2 wherein the signal includes a data stream of image data wherein the high frequency defect data is based on present and previous sample values of the data stream of image data.

8. A system for detecting localized birefringence defects of an object in a dynamic global birefringence field, the system comprising:
   means for generating a digital image of the object including a camera adapted to respond to the birefringence of the object to obtain a signal having high frequency defect data and background birefringence data having a frequency less than the high frequency of the defect data;
   a birefringence filter for filtering the signal to pass the high frequency defect data while eliminating the background birefringence data; and
   an image processor for processing the high frequency defect data to determine the localized birefringence defects in real-time.

9. The system as claimed in claim 8 wherein the filter includes an addressable information storage device.

10. The system as claimed in claim 8 wherein the filter includes a finite impulse response filter.

11. The system as claimed in claim 10 wherein the filter includes a squelch circuit to prevent the filter from producing the filtered high frequency defect data.

12. The system as claimed in claim 11 wherein the squelch circuit includes an addressable information storage device.

13. The system as claimed in claim 8 wherein the object is an optical media substrate.

14. The system as claimed in claim 13 wherein the optical media substrate is an optical disc.

15. The system as claimed in claim 14 wherein the optical disc is an MO disc.

16. The system as claimed in claim 8 wherein the birefringence filter is a digital filter.

17. The system as claimed in claim 8 further comprising a computer coupled to the camera for controlling operation of the camera.

18. The system as claimed in claim 17 wherein the object is an optical media substrate and wherein the system further comprises a motor adapted to move the optical media substrate in response to a control signal from the computer and wherein a plurality of digital images of the optical media substrate are generated and filtered by the birefringence filter.

* * * * *